US00PP36313P2

(12) United States Plant Patent
van Dijk

(10) Patent No.: US PP36,313 P2
(45) Date of Patent: Dec. 10, 2024

(54) ***ANTHURIUM* PLANT NAMED 'AN2437252'**

(50) Latin Name: *Anthurium andreanum*
Varietal Denomination: AN2437252

(71) Applicant: ANTHURA B.V., Bleiswijk (NL)

(72) Inventor: Jan van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 18/607,503

(22) Filed: Mar. 17, 2024

(51) Int. Cl.
*A01H 6/00* (2018.01)
*A01H 5/02* (2018.01)

(52) U.S. Cl.
USPC ..... Plt./367

(58) Field of Classification Search
USPC ..... Plt./367
CPC ..... A01H 6/00; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Anthurium* plant named 'AN2437252', characterized by its upright to outwardly arching and uniform plant habit; freely clumping growth habit; bushy and dense plants; ovate to close to narrowly deltoid dark green-colored leaves; freely flowering habit; inflorescences that are positioned within to slightly above the foliar plane on strong and erect scapes; narrowly ovate light red-colored spathes and yellowish pink-colored spadices; and durable spathes that impart good inflorescence longevity.

2 Drawing Sheets

Figure 1:
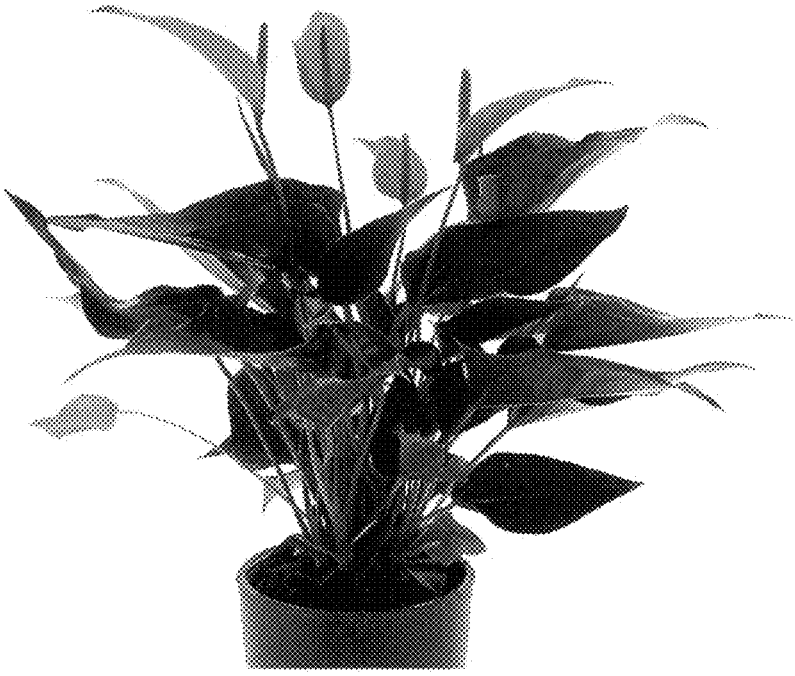

Botanical designation: *Anthurium andreanum.*
Cultivar denomination: 'AN2437252'.

STATEMENT REGARDING PRIOR DISCLOSURES BY INVENTOR and APPLICANT/ASSIGNEE

An European Community Plant Breeder's Rights application for the instant plant was filed by the Applicant/Assignee of the instant application, Anthura B.V. of Bleiswijk, The Netherlands on Nov. 22, 2022, application number 2022/2630. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Anthurium* plant, botanically known as *Anthurium andreanum* and hereinafter referred to by the name 'AN2437252'.

The new *Anthurium* plant is a product of a controlled breeding program conducted by the Inventor in Bleiswijk, The Netherlands. The objective of the breeding program is to create new freely-clumping *Anthurium* plants with attractive, durable and glossy spathes.

The new *Anthurium* plant originated from a cross-pollination made by the Inventor in July 2012 in Bleiswijk, The Netherlands of a proprietary selection of *Anthurium andreanum* identified as code number 10-024278-0001, not patented, as the female, or seed, parent with a proprietary selection of *Anthurium andreanum* identified as code number 09-023494-0005, not patented, as the male, or pollen, parent. The new *Anthurium* was discovered and selected by the Inventor as a single flowering plant within the progeny of the stated cross-pollination in a controlled greenhouse environment in Bleiswijk, The Netherlands in July 2014.

Asexual reproduction of the new *Anthurium* plant by in vitro meristem propagation in a controlled environment in Bleiswijk, The Netherlands since August 2016 has shown that the unique features of this new *Anthurium* are stable and reproduced true to type in successive generations of asexual reproduction.

SUMMARY OF THE INVENTION

Plants of the new *Anthurium* have not been observed under all possible combinations of environmental conditions and cultural practices. The phenotype may vary somewhat with variations in environment conditions such as temperature and light intensity, without, however, any variance in genotype.

The following traits have been repeatedly observed and are determined to be the unique characteristics of 'AN2437252'. These characteristics in combination distinguish 'AN2437252' as a new and distinct *Anthurium* plant:

1. Upright to outwardly arching and uniform plant habit.
2. Freely clumping growth habit; bushy and dense plants.
3. Ovate to close to narrowly deltoid dark green-colored leaves.
4. Freely flowering habit.
5. Inflorescences that are positioned within to slightly above the foliar plane on strong and erect scapes.
6. Narrowly ovate light red-colored spathes and yellowish pink-colored spadices.

7. Durable spathes that impart good inflorescence longevity.

Plants of the new *Anthurium* differ primarily from plants of the female parent selection in the following characteristics:

1. Plants of the new *Anthurium* are more freely clumping than plants of the female parent selection.
2. Spadices of plants of the new *Anthurium* are more tapering than spadices of plants of the female parent selection.

Plants of the new *Anthurium* differ primarily from plants of the male parent selection in the following characteristics:

1. Plants of the new *Anthurium* have smaller spathes than plants of the male parent selection.
2. Spathes of plants of the new *Anthurium* are lighter red in color than spathes of plants of the male parent selection.

Plants of the new *Anthurium* can also be compared to plants of *Anthurium andreanum* 'AN2562165', disclosed in U.S. Plant Pat. No. 34,077. In side-by-side comparisons, plants of the new *Anthurium* differ primarily from plants of 'AN2562165' in spadix color as plants of the new *Anthurium* have light red-colored spadices whereas plants of 'AN2562165' have spadices that are darker red in color. In addition, scapes of plants of the new *Anthurium* are yellowish green in color whereas scapes of plants of 'AN2562165' are yellowish green in color strongly tinged with anthocyanin.

BRIEF DESCRIPTION OF THE PHOTOGRAPHS

The accompanying photographs illustrate the overall appearance of the new *Anthurium*. The photographs show the colors as true as it is reasonably possible to obtain in colored reproductions of this type. Colors in the photographs may differ slightly from the color values cited in the detailed botanical description which accurately describe the colors of the new *Anthurium*.

The photograph on the first sheet (FIG. 1) is a side perspective view of a typical plant of 'AN2437252' grown in a container.

Figure 2:
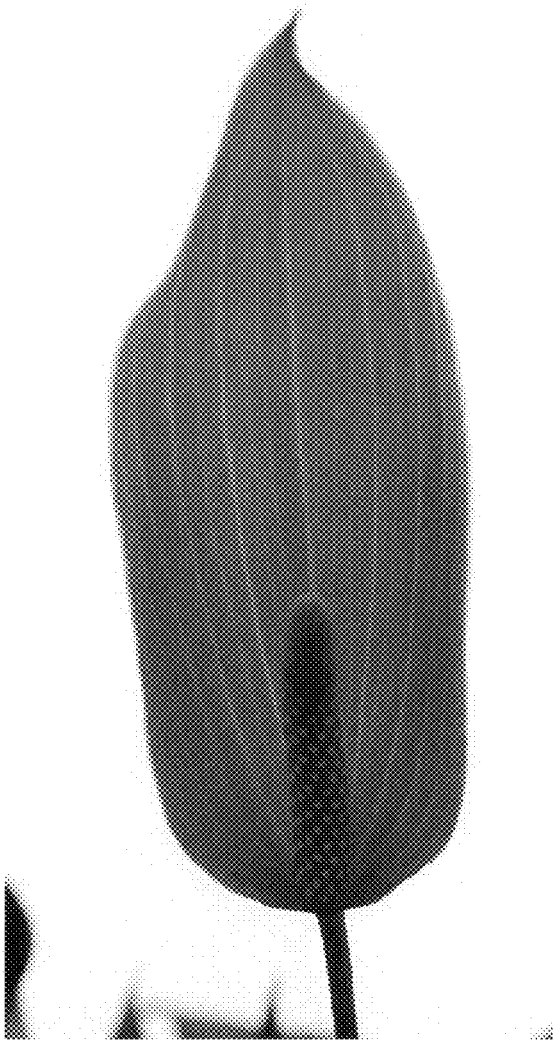

The photograph on the second sheet (FIG. 2) is a close-up view of a typical inflorescence of 'AN2437252'.

DETAILED BOTANICAL DESCRIPTION

The aforementioned photographs and following observations and measurements describe plants grown in 14-cm containers in Bleiswijk, The Netherlands during the autumn in a glass-covered greenhouse. Plants were grown under conditions and practices which approximate those generally used in commercial *Anthurium* production. During the production of the plants, day and night temperatures ranged from about 19° C. to 22.5° C. and light levels ranged from 100 μmol to 200 μmol. Plants were eleven months old when the photographs and the detailed description were taken. In the following description, color references are made to The Royal Horticultural Society Colour Chart, 2015 Edition, except where general terms of ordinary dictionary significance are used.

Botanical classification: *Anthurium andreanum* 'AN2437252'.

Parentage:

*Female, or seed, parent*.—Proprietary selection of *Anthurium andreanum* identified as code number 10-024278-0001, not patented.

*Male, or pollen, parent*.—Proprietary selection of *Anthurium andreanum* identified as code number 09-023494-0005, not patented.

Propagation:

*Type*.—By in vitro meristem propagation.

*Time to initiate roots, summer and winter*.—About two weeks at temperatures about 19° C. to 22.5° C.

*Time to produce a rooted young plant, summer and winter*.—About six to eight weeks at temperatures about 19° C. to 22.5° C.

*Root description*.—Medium in thickness, fibrous; typically creamy white tinged with pink in color, actual color of the roots is dependent on substrate composition, water quality, fertilizer type and formulation, substrate temperature and physiological age of roots.

*Rooting habit*.—Freely branching, medium density.

Plant description:

*Plant shape*.—Upright to outwardly spreading and uniform plant habit; overall shape, broadly obovate to broadly elliptic.

*Growth habit*.—Freely clumping habit with about eight clumps per plant imparting a bushy and dense appearance; moderately vigorous growth habit and moderate growth rate.

*Plant height, from soil level to top of leaf plane*.—About 29.2 cm.

*Plant height, from soil level to top of inflorescences*.—About 34.7 cm.

*Plant diameter or spread*.—About 42.7 cm.

Leaf description:

*Arrangement*.—Alternate; simple; about four leaves per clump.

*Length*.—About 16.8 cm.

*Width*.—About 9.2 cm.

*Shape*.—Ovate to close to narrowly deltoid; slightly to moderately carinate.

*Apex*.—Narrowly apiculate with mucronate apex.

*Base*.—Shallowly and broadly acute to close to truncate.

*Margin*.—Entire; moderately to strongly and coarsely undulate.

*Texture and luster, upper and lower surfaces*.—Smooth, glabrous; moderately leathery; glossy.

*Venation pattern*.—Pinnate.

*Color*.—Developing leaves, upper surface: Slightly darker than a blend of NN137B and 146A. Developing leaves, lower surface: Close to a blend of 146B and 147B. Fully expanded leaves, upper surface: Slightly darker than a blend of NN137A and 147A; venation, close to 143B to 143C. Fully expanded leaves, lower surface: Close to a blend of 146A and 146B; venation, close to 145A.

*Petioles*.—Length: About 12.4 cm. Diameter: Distally, about 3 mm; proximally, about 3.5 mm. Strength: Strong. Texture and luster, upper and lower surfaces: Smooth, glabrous; slightly glossy. Color, upper surface: Close to a blend of 144A and 144B. Color, lower surface: Close to 144B. Geniculum length: About 2.1 cm. Geniculum diameter: About 4 mm. Geniculum texture and luster, upper and lower surfaces: Smooth, glabrous; slightly glossy. Geniculum color, upper surface: Close to 146C. Geniculum color, lower surface: Close to 145A. Wing length:

About 2.8 cm. Wing diameter: About 4 mm. Wing color: Close to 145B; towards the margins, close to 145A.

Inflorescence description:

*Inflorescence arrangement and flowering habit.*—Spathes with spadices held within and slightly above the foliar plane on strong and erect scapes; flowering structures arise from leaf axils; freely and continuous flowering year-round in controlled temperature greenhouses in The Netherlands; typically about eight developing and developed inflorescences per plant at one time; inflorescence development commences about 2.5 to 3.5 months after planting.

Inflorescence longevity: Spathes maintain good substance for about two months on the plant; inflorescences persistent.

*Fragrance*.—None detected.

*Spathes*.—Length: About 10.5 cm. Width: About 4.3 cm. Shape: Narrowly ovate; slightly to moderately concave to slightly axially twisting. Apex: Long apiculate with a mucronate tip. Base: Rounded to shallowly truncate. Margin: Entire; slightly to strongly and coarsely undulate. Aspect: At about 25° to 45° From the peduncle axis. Texture and luster, upper and lower surfaces: Smooth, glabrous; moderately leathery; glossy. Color: When developing, front surface: Close to 41A. When developing, rear surface: Close to 39B; venation, close to 146B. Fully developed, front surface: Close to a blend of 39B and 43C; towards the apex, close to 43B; venation, close to 197A; with subsequent development, color becoming closer to 51B to 51C with venation, close to 197A. Fully developed, rear surface: Close to 49A to 49C with apex, close to 150A; towards the base, close to 144A; venation, close to 197A and proximally, close to 143A; with subsequent development, color becoming closer to 51C, towards the apex, close to 152B and 152C, and towards the base, tinged with close to 160B.

*Spadices*.—Length: About 4.3 cm. Diameter: About 7.5 mm. Shape: Columnar, slightly tapering towards the apex; apex, obtuse; base, obtuse; in cross-section, rounded. Aspect: About 45° From spathe axis and about 10° From the peduncle axis. Color: Immature: Close to 43D and distally, close to 41C. Mature: Close to 31D and distally, close to 38A. Flowers: Type: Hermaphroditic. Quantity per spadix: Numerous, about 160. Height: Less than 0.5 mm. Diameter: About 2.5 mm. Shape: Roughly square. Anther color: Close to 31D. Pollen amount: None observed. Stigma color: Close to N155C.

*Scape*.—Length: About 21.7 cm. Diameter: About 3.5 mm. Strength: Strong. Aspect: About 10° From vertical. Color: Close to 145A and distally, close to 146D.

*Seed and fruit*.—To date, seed and fruit development has not been observed on plants of the new *Anthurium*.

Pathogen & pest resistance: To date, plants of the new *Anthurium* have not been observed to be resistant to pathogens or pests common to *Anthurium* plants.

Temperature tolerance: Plants of the new *Anthurium* have been observed to be tolerant to high temperatures about 30° C. and to be hardy to USDA Hardiness Zone 10.

It is claimed:

1. A new and distinct *Anthurium* plant named 'AN2437252' as illustrated and described.

* * * * *